US010537634B2

(12) United States Patent
Garry et al.

(10) Patent No.: US 10,537,634 B2
(45) Date of Patent: *Jan. 21, 2020

(54) IMMUNOGENIC PEPTIDE COMPOSITION AND METHOD

(71) Applicants: THE ADMINISTRATORS OF THE TULANE EDUCATIONAL FUND, New Orleans, LA (US); AUTOIMMUNE TECHNOLOGIES, LLC., New Orleans, LA (US)

(72) Inventors: Robert Francis Garry, New Orleans, LA (US); Russell B. Wilson, Mandeville, LA (US)

(73) Assignees: THE ADMINISTRATORS OF THE TULANE EDUCATIONAL FUND, New Orleans, LA (US); AUTOIMMUNE TECHNOLOGIES, LLC, New Orleans, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/176,743

(22) Filed: Oct. 31, 2018

(65) Prior Publication Data

US 2019/0054168 A1 Feb. 21, 2019

Related U.S. Application Data

(60) Continuation of application No. 15/591,386, filed on May 10, 2017, now Pat. No. 10,137,194, which is a division of application No. 13/828,988, filed on Mar. 14, 2013, now Pat. No. 9,649,375.

(51) Int. Cl.

| | |
|---|---|
| ***A61K 39/395*** | (2006.01) |
| ***C07K 17/02*** | (2006.01) |
| ***C07K 16/10*** | (2006.01) |
| ***A61K 39/12*** | (2006.01) |
| ***C07K 14/005*** | (2006.01) |
| ***A61K 39/00*** | (2006.01) |

(52) U.S. Cl.

CPC .......... *A61K 39/3955* (2013.01); *A61K 39/12* (2013.01); *C07K 14/005* (2013.01); *C07K 16/1018* (2013.01); *C07K 17/02* (2013.01); *A61K 2039/6081* (2013.01); *C07K 2317/33* (2013.01); *C12N 2760/16122* (2013.01); *C12N 2760/16134* (2013.01)

(58) Field of Classification Search

CPC ................ A61K 39/3955; A61K 39/12; A61K 2039/6081; A61K 38/00; A61K 38/162; A61K 2039/6075; A61K 2039/525; C07K 14/005; C07K 16/1018; C07K 17/02; C07K 2317/33; C07K 7/06; C07K 7/08; C07K 2319/00; C07K 14/08; C12N 2760/16134; C12N 2760/16122; C12N 7/00; C12N 2760/16151

See application file for complete search history.

(56) References Cited

U.S. PATENT DOCUMENTS

| | | | |
|---|---|---|---|
| 5,589,174 | A | 12/1996 | Okuno et al. |
| 5,606,030 | A | 2/1997 | Emini et al. |
| 5,824,307 | A | 10/1998 | Johnson |
| 6,068,973 | A | 5/2000 | Barney et al. |
| 6,800,738 | B1 | 10/2004 | Carter et al. |
| 7,070,775 | B2 | 7/2006 | Le et al. |
| 7,087,409 | B2 | 8/2006 | Barbas, III et al. |
| 7,456,260 | B2 | 11/2008 | Rybak et al. |
| 7,479,285 | B1 | 1/2009 | Van Nest et al. |
| 7,491,793 | B2 | 2/2009 | Garry et al. |
| 7,807,161 | B2 | 10/2010 | Yamamoto et al. |
| 8,222,204 | B2 | 7/2012 | Garry et al. |
| 8,598,116 | B2 | 12/2013 | Garry et al. |
| 8,604,165 | B2 | 12/2013 | Garry et al. |
| 2003/0180328 | A1 | 9/2003 | Bogoch et al. |
| 2006/0280754 | A1 | 12/2006 | Garry et al. |
| 2009/0169576 | A1 | 7/2009 | Crea et al. |

(Continued)

FOREIGN PATENT DOCUMENTS

| | | | | |
|---|---|---|---|---|
| WO | WO-2007047831 A2 * | 4/2007 | | .......... A61K 39/145 |
| WO | 2009002516 A1 | 12/2008 | | |

(Continued)

OTHER PUBLICATIONS

Krammer F, Schinko T, Messner P, Palmberger D, Ferko B, Grabherr R. Influenza virus-like particles as an antigen-carrier platform for the ESAT-6 epitope of *Mycobacterium tuberculosis*. J Virol Methods. Jul. 2010;167(1):17-22. Epub Mar. 19, 2010.*

(Continued)

*Primary Examiner* — Rachel B Gill

(74) *Attorney, Agent, or Firm* — Olson & Cepuritis, Ltd.

(57) ABSTRACT

Immunogenic influenza hemagglutinin-derived peptide compositions described herein induce a specific therapeutic antibody response against influenza virus. The immunogenic peptide compositions comprise a segment from the fusion initiation region (FIR) domain of an influenza hemagglutinin protein bound to an immunogenic carrier protein, such as an influenza hemagglutinin (HA) protein (i.e., full length HA), and the like. The immunogenic peptide compositions described herein can be utilized to treat or prevent influenza infection and to prepare influenza-specific therapeutic antibodies that interfere with influenza virus-host cell membrane fusion. The peptide conjugates can be formulated in pharmaceutical compositions useful for broad spectrum treatment or prevention of influenza infections.

20 Claims, 2 Drawing Sheets

Specification includes a Sequence Listing.

(56) References Cited

U.S. PATENT DOCUMENTS

| | | | |
|---|---|---|---|
| 2009/0234096 | A1 | 9/2009 | Garry et al. |
| 2010/0152109 | A1 | 6/2010 | Garry et al. |
| 2010/0297174 | A1 | 11/2010 | Garcia-Sastre et al. |
| 2011/0059472 | A1 | 3/2011 | Li |
| 2012/0009212 | A1 | 1/2012 | Hodges |
| 2012/0070455 | A1 | 3/2012 | He et al. |
| 2012/0289458 | A1 | 11/2012 | Garry et al. |
| 2014/0194347 | A1 | 7/2014 | Garry et al. |

FOREIGN PATENT DOCUMENTS

| | | | |
|---|---|---|---|
| WO | 2010124393 | A1 | 11/2010 |
| WO | 2010130636 | A1 | 11/2010 |
| WO | 2013007770 | A1 | 1/2013 |

OTHER PUBLICATIONS

Autoimmune Technologies, LLC, "New Influenza Drug Wins QTDP Grant", Press Release, Nov. 16, 2010.

Autoimmune Technologies, LLC, "FF-3, The First Cell-Entry-Inhibiting Influenza Drug", http:///www.autoimmune.com/ FF-3. html., online, May 11, 2012.

Autoimmune Technologies, LLC, Safety Study of Flufirvitide-3 Nasal Spray in Healthy Subjects, ClinicalTrials.gov. Trial Identifier: NCT01313962, https://clinicaltrials.gov/ct2/results (2012).

Badani, H. et al., Mechanism and Action of Flufirvitide, A Peptide Inhibitor of Influenza Virus Infection, Biophysical 100:216a, Biophysical Society Meeting, Baltimore, MD (2011).

Badani, H. et al., Mechanism and Action of Flufirvitide-3 (FF3), A Peptide Inhibitor of Influenza Virus Infection, Biophysical Society Meeting, San Francisco, CA (2014).

Badani, H. et al., Peptide Entry Inhibitors of Enveloped Viruses: The Importance of Interfacial Hydrophobicity, Biochimica et Biophysica Acta 1838, 2180-2197 (2014).

Brandon, David L. et al., 2-Morpholinoethylisocyanide as a Coupling Agent for Hapten-Protein Conjugates, Food and Agricultural Immunology 17 (1), 53-61 (2006).

CDC, Vaccine Effectiveness—How Well Does the Flu Vaccine Work?, http://cdc.gov/flu/about (2014).

Corti, D. et al., A Neutralizing Antibody Selected From Plasma Cells That Binds to Group 1 and Group 2 Influenza A Hemagglutinins, Science 333, 6044, 850-856 (2011).

Ekiert, D.C. et al., A Highly Conserved Neutralizing Epitope on Group 2 Influenza A Viruses, Science 333 (6044), 843-850 (2011).

Fan, Jiang et al., Preclinical Study of Influenza Virus A M2 Peptide Conjugate Vaccines in Mice, Ferrets, and Rhesus Monkeys, Vaccine 22, 2993-3003 (2004).

Gao, W. et al., Protection of Mice and Poultry From Lethal H5N1 Avian Influenza Virus Through Adenovirus-Based Immunization, J. Virol. 80 (4) 1959-1964 (2006).

Huang, Jen-Min et al., Immunostimulatory Activity of Bacillus Spores, FEMS Immunol Med Microbiol 53, 195-203 (2008).

Janulikova, J. et al., Two Distinct Regions of HA2 Glycopolypeptide of Influenza Virus Hemagglutinin Elicit Cross-Protective Immunity Against Influenza, Acta Virol. 56(3): 169-176 (2012).

Magadan, J.G. et al., Influenza A Virus Hemagglutinin Trimerization Completes Monomer Folding and Antigenicity, Journal of Virology 87 (17), 9742-9753 (2013).

Naveen, S. et al., Peptide Based Inhibitors of Pandemic Influenza Virus in Ferrets, Atlanta, GA Symposium entitled Swine Origin H1N1 Virus: The First Pandemic of the 21st Century, (2010).

Sigma-Aldrich, Product Information: Maleimide Activated BSA, KLH Conjugation Kit. Cat# MBK1, http://www.sigmaaldrich.com/content/dam/sigma-aldrich/docs/Sigma/Bulletin. Updated (2012).

Stanekova, Z. et al., Heterosubtypic Protective Immunity Against Influenza A Virus Induced by Fusion Peptide of the Hemagglutinin in Comparison to Ectodomain of M2 Protein, Acta Virol. 55 (1), 61-67 (2011).

Wang, Taia T. et al., Vaccination with a Synthetic Peptide From the Influenza Virus Hemagglutinin Provides Protection Against Distinct Viral Subtypes, PNAS 107 (44), 18979-18984 (2010).

* cited by examiner

Family: Arenavirus    Coronavirus    Filovirus    Orthomyxovirus    Paramyxovirus    Retrovirus
Example: Lassa       SARS           Ebola        Influenza          Measles          HIV-1 TM
         virus GP2   coronavirus S2 virus GP2    virus HA2          virus F1

Legend:
- fusion peptide
- N-helix
- FIR
- C-helix
- aromatic
- anchor

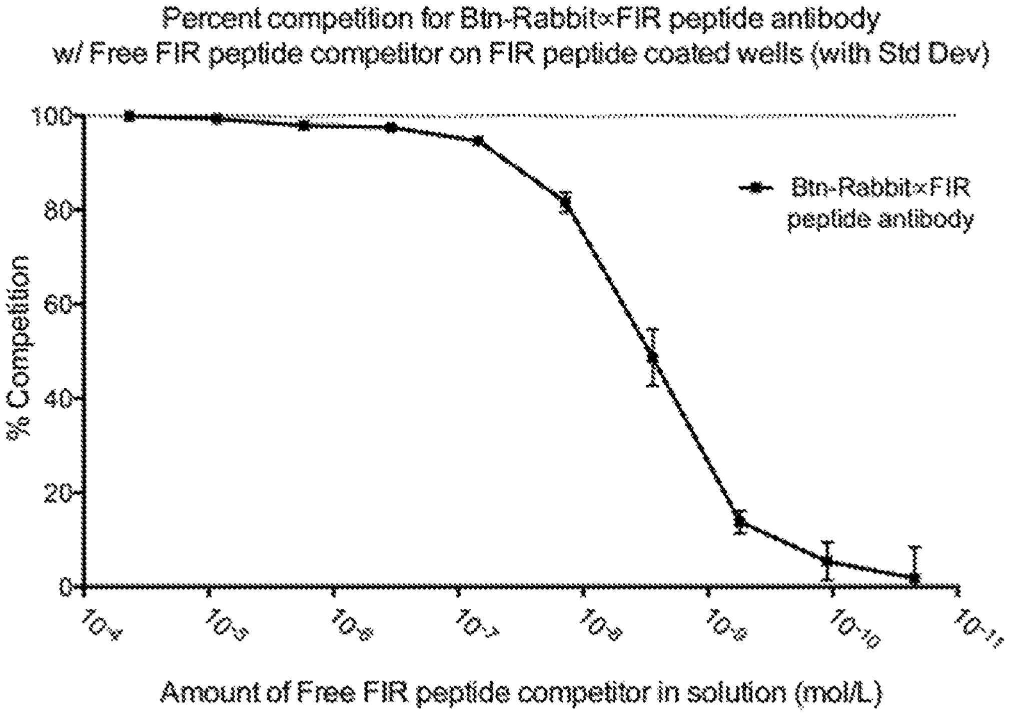

FIG. 2

Percent competition for Btn-Rabbit×FIR peptide antibody w/ Free FIR peptide competitor on FIR peptide coated wells (with Std Dev)

— Btn-Rabbit×FIR peptide antibody

% Competition vs. Amount of Free FIR peptide competitor in solution (mol/L)

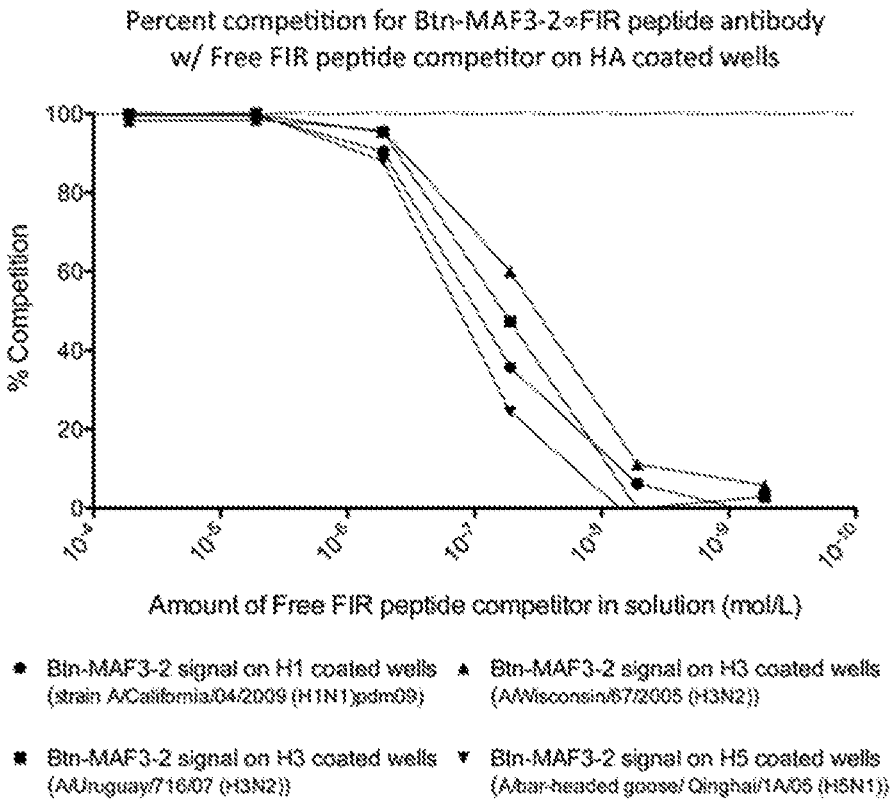

FIG. 3

Percent competition for Btn-MAF3-2×FIR peptide antibody w/ Free FIR peptide competitor on HA coated wells % Competition vs. Amount of Free FIR peptide competitor in solution (mol/L)

- Btn-MAF3-2 signal on H1 coated wells (strain A/California/04/2009 (H1N1)pdm09)
- Btn-MAF3-2 signal on H3 coated wells (A/Wisconsin/67/2005 (H3N2))
- Btn-MAF3-2 signal on H3 coated wells (A/Uruguay/716/07 (H3N2))
- Btn-MAF3-2 signal on H5 coated wells (A/bar-headed goose/Qinghai/1A/05 (H5N1))

SEQUENCE LISTING

```
<160> NUMBER OF SEQ ID NOS: 19

<210> SEQ ID NO 1
<211> LENGTH: 16
<212> TYPE: PRT
<213> ORGANISM: Influenza A virus
<220> FEATURE:
<223> OTHER INFORMATION: Residues 84-99 of influenza A/H3 hemagglutinin
      2

<400> SEQUENCE: 1
```

```
Val Glu Asp Thr Lys Ile Asp Leu Trp Ser Tyr Asn Ala Glu Leu Leu
1               5                   10                  15


<210> SEQ ID NO 2
<211> LENGTH: 222
<212> TYPE: PRT
<213> ORGANISM: Influenza A virus
<220> FEATURE:
<223> OTHER INFORMATION: Influenza A/H3 hemagglutinin 2

<400> SEQUENCE: 2

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Asp Gln Gly Ser
            20                  25                  30

Gly Tyr Ala Ala Asp Lys Glu Ser Thr Gln Lys Ala Phe Asp Gly Ile
        35                  40                  45

Thr Asn Lys Val Asn Ser Val Ile Glu Lys Met Asn Thr Gln Phe Glu
    50                  55                  60

Ala Val Gly Lys Glu Phe Ser Asn Leu Glu Arg Arg Leu Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Tyr Asp Lys Val Arg Met Gln Leu Arg Asp
        115                 120                 125

Asn Val Lys Glu Leu Gly Asn Gly Cys Phe Glu Phe Tyr His Lys Cys
    130                 135                 140

Asp Asp Glu Cys Met Asn Ser Val Lys Asn Gly Thr Tyr Asp Tyr Pro
145                 150                 155                 160

Lys Tyr Glu Glu Glu Ser Lys Leu Asn Arg Asn Glu Ile Lys Gly Val
                165                 170                 175

Lys Leu Ser Ser Met Gly Val Tyr Gln Ile Leu Ala Ile Tyr Ala Thr
            180                 185                 190

Val Ala Gly Ser Leu Ser Leu Ala Ile Met Met Ala Gly Ile Ser Phe
        195                 200                 205

Trp Met Cys Ser Asn Gly Ser Leu Gln Cys Arg Ile Cys Ile
    210                 215                 220


<210> SEQ ID NO 3
<211> LENGTH: 16
<212> TYPE: PRT
<213> ORGANISM: Influenza A virus
<220> FEATURE:
<223> OTHER INFORMATION: Residues 84-99 of influenza A/H1 hemagglutinin
      2

<400> SEQUENCE: 3

Val Asp Asp Gly Phe Leu Asp Ile Trp Thr Tyr Asn Ala Glu Leu Leu
1               5                   10                  15


<210> SEQ ID NO 4
<211> LENGTH: 16
<212> TYPE: PRT
<213> ORGANISM: Influenza A virus
<220> FEATURE:
<223> OTHER INFORMATION: Residues 84-99 of influenza A/H5 hemagglutinin
      2
```

<400> SEQUENCE: 4

Met Glu Asp Gly Phe Leu Asp Val Trp Thr Tyr Asn Ala Glu Leu Leu
1 5 10 15

<210> SEQ ID NO 5
<211> LENGTH: 16
<212> TYPE: PRT
<213> ORGANISM: Influenza A virus
<220> FEATURE:
<223> OTHER INFORMATION: Residues 84-99 of influenza A/H7 hemagglutinin 2

<400> SEQUENCE: 5

Thr Arg Asp Ala Met Thr Glu Val Trp Ser Tyr Asn Ala Glu Leu Leu
1 5 10 15

<210> SEQ ID NO 6
<211> LENGTH: 16
<212> TYPE: PRT
<213> ORGANISM: Influenza A virus
<220> FEATURE:
<223> OTHER INFORMATION: Residues 84-99 of influenza A/H9 hemagglutinin 2

<400> SEQUENCE: 6

Val Asp Asp Gln Ile Gln Asp Ile Trp Ala Tyr Asn Ala Glu Leu Leu
1 5 10 15

<210> SEQ ID NO 7
<211> LENGTH: 16
<212> TYPE: PRT
<213> ORGANISM: Influenza A virus
<220> FEATURE:
<223> OTHER INFORMATION: Residues 84-99 of influenza A/H2 and A/H6 hemagglutinin 2

<400> SEQUENCE: 7

Met Glu Asp Gly Phe Leu Asp Val Trp Thr Tyr Asn Ala Glu Leu Leu
1 5 10 15

<210> SEQ ID NO 8
<211> LENGTH: 16
<212> TYPE: PRT
<213> ORGANISM: Influenza A virus
<220> FEATURE:
<223> OTHER INFORMATION: Residues 84-99 of influenza A/H10 hemagglutinin 2

<400> SEQUENCE: 8

Thr Lys Asp Ser Ile Thr Asp Ile Trp Thr Tyr Asn Ala Glu Leu Leu
1 5 10 15

<210> SEQ ID NO 9
<211> LENGTH: 16
<212> TYPE: PRT
<213> ORGANISM: Influenza A virus
<220> FEATURE:
<223> OTHER INFORMATION: Residues 84-99 of influenza A/H13 hemagglutinin 2

<400> SEQUENCE: 9

Ile Asp Asp Ala Val Thr Asp Ile Trp Ser Tyr Asn Ala Lys Leu Leu
1 5 10 15

<210> SEQ ID NO 10
<211> LENGTH: 16
<212> TYPE: PRT

<213> ORGANISM: Influenza A virus
<220> FEATURE:
<223> OTHER INFORMATION: Residues 84-99 of influenza A/H15 hemagglutinin
2

<400> SEQUENCE: 10

Thr Arg Asp Ser Leu Thr Glu Ile Trp Ser Tyr Asn Ala Glu Leu Leu
1 5 10 15

<210> SEQ ID NO 11
<211> LENGTH: 16
<212> TYPE: PRT
<213> ORGANISM: Influenza A virus
<220> FEATURE:
<223> OTHER INFORMATION: Residues 84-99 of influenza A/H16 hemagglutinin
2

<400> SEQUENCE: 11

Val Asp Asp Ala Val Thr Asp Ile Trp Ser Tyr Asn Ala Lys Leu Leu
1 5 10 15

<210> SEQ ID NO 12
<211> LENGTH: 16
<212> TYPE: PRT
<213> ORGANISM: Influenza B virus
<220> FEATURE:
<223> OTHER INFORMATION: Residues 84-99 of influenza A hemagglutinin
2/H17

<400> SEQUENCE: 12

Val Asp Asp Ala Leu Leu Asp Ile Trp Ser Tyr Gln Thr Glu Leu Leu
1 5 10 15

<210> SEQ ID NO 13
<211> LENGTH: 566
<212> TYPE: PRT
<213> ORGANISM: Influenza A virus
<220> FEATURE:
<223> OTHER INFORMATION: Influenza A/H1 hemagglutinin

<400> SEQUENCE: 13

Met Lys Thr Ile Ile Ala Phe Ser Cys Ile Leu Cys Leu Ile Phe Ala
1 5 10 15

Gln Lys Leu Pro Gly Ser Asp Asn Ser Met Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Ser Ser Thr
50 55 60

Gly Arg Ile Cys Asn Ser Pro His Gln Ile Leu Asp Gly Lys Asn Cys
65 70 75 80

Thr Leu Ile Asp Ala Leu Leu Gly Asp Pro His Cys Asp Asp Phe Gln
85 90 95

Asn Lys Glu Trp Asp Leu Phe Val Glu Arg Ser Thr Ala Tyr Ser Asn
100 105 110

Cys Tyr Pro Tyr Tyr Val Pro Asp Tyr Ala Thr Leu Arg Ser Leu Val
115 120 125

Ala Ser Ser Gly Asn Leu Glu Phe Thr Gln Glu Ser Phe Asn Trp Thr
130 135 140

Gly Val Ala Gln Asp Gly Ser Ser Tyr Ala Cys Arg Arg Gly Ser Val
145 150 155 160

Asn Ser Phe Phe Ser Arg Leu Asn Trp Leu Tyr Asn Leu Asn Tyr Lys

-continued

```
                165                 170                 175

Tyr Pro Glu Gln Asn Val Thr Met Pro Asn Asn Asp Lys Phe Asp Lys
            180                 185                 190

Leu Tyr Ile Trp Gly Val His His Pro Gly Thr Asp Lys Asp Gln Thr
        195                 200                 205

Asn Leu Tyr Val Gln Ala Ser Gly Arg Val Ile Val Ser Thr Lys Arg
    210                 215                 220

Ser Gln Gln Thr Val Ile Pro Asn Ile Gly Ser Arg Pro Trp Val Arg
225                 230                 235                 240

Gly Val Ser Ser Ile Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Gln Ser Gly Lys Ser Ser Ile Met Arg Ser Asp Ala
        275                 280                 285

His Ile Asp Glu Cys Asn Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Thr Gly Lys Leu Asn Arg Val
385                 390                 395                 400

Ile Lys Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Ser Lys Leu Phe
    450                 455                 460

Glu Arg Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Ile Tyr Arg Asn Glu Ala Leu
            500                 505                 510

Asn Asn Arg Phe Gln Ile Lys Gly Val Gln Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565
```

<210> SEQ ID NO 14

```
<211> LENGTH: 562
<212> TYPE: PRT
<213> ORGANISM: Influenza A virus
<220> FEATURE:
<223> OTHER INFORMATION: Influenza A/H2 hemagglutinin

<400> SEQUENCE: 14

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Asn Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Glu Gly Ser Asp Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Ile Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Thr Arg Pro Lys Val Asn Gly Gln Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380
```

```
Phe Asp Gly Ile Thr Asn Lys Val Asn Ser Val Ile Glu Lys Met Asn
385                 390                 395                 400

Thr Gln Phe Glu Ala Val Gly Lys Glu Phe Gly Asn Leu Glu Arg Arg
                405                 410                 415

Leu Glu Asn Leu Asn Lys Arg Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile
```

```
<210> SEQ ID NO 15
<211> LENGTH: 566
<212> TYPE: PRT
<213> ORGANISM: Influenza A virus
<220> FEATURE:
<223> OTHER INFORMATION: Influenza A/H3 hemagglutinin

<400> SEQUENCE: 15

Met Glu Ala Lys Leu Phe Val Leu Phe Cys Thr Phe Thr Val Leu Lys
1               5                   10                  15

Ala Asp Thr Ile Cys Val Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Ser Leu Asn Gly Ile
    50                  55                  60

Ala Pro Leu Gln Leu Gly Lys Cys Asn Val Ala Gly Trp Leu Leu Gly
65                  70                  75                  80

Asn Pro Glu Cys Asp Leu Leu Leu Thr Ala Asn Ser Trp Ser Tyr Ile
                85                  90                  95

Ile Glu Thr Ser Asn Ser Glu Asn Gly Thr Cys Tyr Pro Gly Glu Phe
            100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Ala Ser Ser Trp Pro Asn His Glu
    130                 135                 140

Thr Thr Lys Gly Val Thr Ala Ala Cys Ser Tyr Ser Gly Ala Ser Ser
145                 150                 155                 160

Phe Tyr Arg Asn Leu Leu Trp Ile Thr Lys Lys Gly Thr Ser Tyr Pro
                165                 170                 175
```

-continued

```
Thr Leu Ser Lys Ser Tyr Thr Asn Asn Lys Gly Lys Glu Val Leu Val
            180                 185                 190

Leu Trp Gly Val His His Pro Pro Thr Val Asn Glu Gln Gln Ser Leu
        195                 200                 205

Tyr Gln Asn Ala Asp Ala Tyr Val Ser Val Gly Ser Ser Lys Tyr Asn
    210                 215                 220

Arg Arg Phe Thr Pro Glu Ile Ala Ala Arg Pro Lys Val Arg Gly Gln
225                 230                 235                 240

Ala Gly Arg Met Asn Tyr His Trp Thr Leu Leu Asp Gln Gly Asp Thr
                245                 250                 255

Ile Thr Phe Glu Ala Thr Gly Asn Leu Ile Ala Pro Trp Tyr Ala Phe
            260                 265                 270

Ala Leu Asn Lys Gly Ser Asp Ser Gly Ile Ile Thr Ser Asp Ala Pro
        275                 280                 285

Val His Asn Cys Asp Thr Arg Cys Gln Thr Pro His Gly Ala Leu Asn
    290                 295                 300

Ser Ser Leu Pro Phe Gln Asn Val His Pro Ile Thr Ile Gly Glu Cys
305                 310                 315                 320

Pro Lys Tyr Val Lys Ser Thr Lys Leu Arg Met Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Lys Phe Thr Ala Val Gly Lys Glu Phe Asn Asn
                405                 410                 415

Leu Glu Arg Arg Ile Glu Asn Leu Asn Lys Lys Val Asp Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Phe His Asp Ser Asn Val Arg Asn Leu Tyr Glu
    450                 455                 460

Lys Val Lys Ser Gln Leu Arg Asn Asn Ala Lys Glu Leu Gly Asn Gly
465                 470                 475                 480

Cys Phe Glu Phe Tyr His Lys Cys Asp Asp Glu Cys Ile Glu Ser Val
                485                 490                 495

Lys Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 16
<211> LENGTH: 568
<212> TYPE: PRT

```
<213> ORGANISM: Influenza A virus
<220> FEATURE:
<223> OTHER INFORMATION: Influenza A/H5 hemagglutinin

<400> SEQUENCE: 16

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Leu Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asn His Glu Ala Ser
    130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Leu Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Thr
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
```

-continued

```
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Gly Leu Gly
465                 470                 475                 480

Asn Gly Cys Phe Glu Phe Tyr His Lys Cys Asp Asn Glu Cys Met Glu
                485                 490                 495

Ser Val Lys Asn Gly Thr Tyr Asp Tyr Pro Gln Tyr Ser Glu Glu Ala
            500                 505                 510

Arg Leu Asn Arg Glu Glu Ile Ser Gly Val Lys Leu Glu Ser Met Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565


<210> SEQ ID NO 17
<211> LENGTH: 560
<212> TYPE: PRT
<213> ORGANISM: Influenza A virus
<220> FEATURE:
<223> OTHER INFORMATION: Influenza A/H7 hemagglutinin

<400> SEQUENCE: 17

Met Asn Thr Gln Ile Leu Val Phe Ala Leu Val Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Val Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Thr Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asp Pro Ala Leu Ile Ile Trp Gly Ile His
```

-continued

```
            180                 185                 190

His Ser Gly Ser Thr Thr Glu Gln Thr Lys Leu Tyr Gly Ser Gly Asn
        195                 200                 205

Lys Leu Ile Thr Val Gly Ser Ser Asn Tyr Gln Gln Ser Phe Val Pro
    210                 215                 220

Ser Pro Glu Ala Arg Pro Gln Val Asn Gly Gln Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Val Thr Gly Lys Leu Asn Arg Leu Ile Glu Lys Thr Asn Gln
385                 390                 395                 400

Gln Phe Lys Leu Ile Asp Asn Glu Phe Thr Glu Val Glu Lys Gln Ile
                405                 410                 415

Gly Asn Val Ile Asn Trp Thr Arg Asp Ser Met Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asn Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Ala Met Gly Leu
    530                 535                 540

Val Phe Ile Cys Val Lys Asn Gly Asn Met Arg Cys Thr Ile Cys Ile
545                 550                 555                 560
```

<210> SEQ ID NO 18
<211> LENGTH: 9
<212> TYPE: PRT
<213> ORGANISM: Artificial Sequence
<220> FEATURE:
<223> OTHER INFORMATION: Sythetic peptide linker -continued

```
<400> SEQUENCE: 18

Asp Tyr Lys Lys Asp Asp Asp Asp Lys
1               5


<210> SEQ ID NO 19
<211> LENGTH: 17
<212> TYPE: PRT
<213> ORGANISM: Artificial Sequence
<220> FEATURE:
<223> OTHER INFORMATION: Sythetic FIR peptide linked to Cys

<400> SEQUENCE: 19

Cys Val Glu Asp Thr Lys Ile Asp Leu Trp Ser Tyr Asn Ala Glu Leu
1               5                   10                  15

Leu
```

IMMUNOGENIC PEPTIDE COMPOSITION AND METHOD

CROSS-REFERENCE TO RELATED APPLICATIONS

This application is a continuation of U.S. application Ser. No. 15/591,386, filed on May 10, 2017, which is a division of U.S. application Ser. No. 13/828,988, filed on Mar. 14, 2013, now U.S. Pat. No. 9,649,375, each of which is incorporated herein by reference in its entirety.

FIELD OF INVENTION

The present invention relates to immunogenic influenza hemagglutinin A2 (HA2)-derived peptide compositions and methods of inducing a specific antibody response against influenza virus using the compositions.

SEQUENCE LISTING INCORPORATION

Biological sequence information for this application is included in an ASCII text file, filed with the application, having the file name "TU-271-5-SEQ.txt", created on Mar. 14, 2013, and having a file size of 29,368 bytes, which is incorporated herein by reference.

BACKGROUND OF THE INVENTION

Hemagglutinin (HA) is an envelope protein of the influenza virus (an orthomyxovirus), and is the prototypic RNA virus Class I fusion protein. HA is produced in infected cells as a precursor protein HA0 which is proteolytically cleaved into 2 proteins referred to as HA1 and HA2. HA2 contains an amino terminal hydrophobic domain, referred to as the fusion peptide, which is exposed during cleavage of the hemagglutinin precursor protein. Retroviral transmembrane proteins contain several structural features in common with the known structure of HA2 in addition to the fusion peptide, including an extended amino-terminal helix (N-helix, usually a "heptad repeat" or "leucine zipper"), a carboxy-terminal helix (C-helix), and an aromatic motif proximal to the transmembrane domain. The presence of at least four out of these five domains defines a viral envelope protein as a Class I fusion protein.

FIG. 1 shows six identified domains of the fusion proteins of the six families of Class I viruses. The fusion proteins originate in a hydrophobic fusion peptide, terminate in an anchor peptide, and incorporate an extended amino terminal alpha-helix (N-helix, usually a "heptad repeat" or "leucine zipper"), a carboxy-terminal alpha-helix (C-helix), and sometimes an aromatic motif proximal to the virion envelope. The sixth domain, referred to herein as the fusion initiation region (FIR), which is disclosed in U.S. Pat. Nos. 7,491,793 and 8,222,204 (to Garry and Wilson), each of which is incorporated herein by reference in its entirety.

There are multiple subtypes of the influenza A virus. Each viral subtype comprises one specific combination of versions of two glycoproteins that are embedded in the lipid membrane envelopes of the viruses. The two subtype-defining glycoproteins are hemagglutinin HA and neuraminidase (NA). There are seventeen known variants of HA, which are referred to as H1 through H17, respectively, and nine known variants of neuraminidase, which are referred to as N1 through N9, respectively. Each viral subtype is specified characterized by its hemagglutinin and neuraminidase variant numbers, respectively. For example, influenza A subtype H3N2 is a swine flu, and subtype H5N1 is an avian flu.

About 10 to 20 percent of the population of the United States suffers from seasonal influenza each year. While most individuals recover from influenza in one to two weeks, the very young, the elderly, and persons with chronic medical conditions can develop post-flu pneumonia and other lethal complications. The causative agent of influenza is the influenza virus, an orthomyxovirus that readily develops new strains through a process of reassortment and mutation of the segmented viral genome.

The FIR of Class I viruses is the region of the viral fusion envelope proteins involved in virus envelope-to-host cell membrane fusion, which is the process by which a host cell membrane-bound virus interrupts the integrity of the host cell membrane to inject the genetic material of the virus into the host cell. This process involves a merger of the viral envelope and a host cell membrane, which is mediated by the viral fusion protein (e.g., hemagglutinin in the case of influenza viruses), thus exposing the interior of the host cell to the interior of the virus. As disclosed in U.S. Pat. Nos. 7,491,793 and 8,222,204 (to Garry and Wilson) mentioned above, relatively short peptides comprising or consisting of a segment of the FIR can bind to a virus fusion protein and interfere with conformational changes required for fusion to occur. Such peptides thus prevent infection of the host cells by the viruses, despite the fact that the viruses can still bind to the surface of the host cell membrane. Thus, the FIR peptides inhibit viral infectivity by an entirely different mechanism than traditional vaccine treatments, which generally involve production of antibodies that prevent binding of the virus with the host cell, rather than interfering with the biochemical events that comprise the vial fusion mechanism, per se.

Highly virulent strains of type A influenza virus can produce epidemics and pandemics. In recent years, there has been an emergence of a highly pathogenic strain of avian influenza A virus subtype H5N1 capable of inflicting a high mortality rate. Dealing with the threats posed by the influenza virus both to public health and as a potential agent of bioterrorism are high priorities. Consequently, there is an ongoing need to develop treatment compositions and methods to control seasonal influenza and the increasing threat of pandemic influenza and weaponized influenza. The peptide conjugates, antibodies, and described herein address these needs.

SUMMARY OF THE INVENTION

Immunogenic influenza hemagglutinin-derived peptide conjugates described herein induce a specific therapeutic antibody response against influenza virus. The immunogenic peptide conjugates comprise a hemagglutinin FIR peptide (i.e., a segment from the fusion initiation region (FIR) domain of an influenza hemagglutinin protein) conjugated to an immunogenic carrier protein. The hemagglutinin FIR peptide consists of SEQ ID NO: 1 (residues 84 to 99 of SEQ ID NO: 2, which is a representative sequence of influenza A, subtype H3 hemagglutinin 2), or a variant thereof. The immunogenic peptide conjugates described herein are useful for treating or preventing influenza infections and for eliciting influenza-specific therapeutic antibodies that interfere with influenza virus-host cell membrane fusion. The peptide conjugates can be formulated in pharmaceutical compositions useful for treating or preventing a broad spectrum of influenza infections.

The immunogenic peptide conjugates described herein can be utilized to treat or prevent influenza infection and to elicit influenza-specific therapeutic antibodies that interfere with influenza virus-host cell fusion. The peptide conjugates can be formulated in pharmaceutical compositions useful for treating or preventing influenza infections in combination with a pharmaceutically acceptable carrier, and optionally including one or more adjuvants, excipients, and the like.

The immunogenic carrier protein portion of the immunogenic peptide conjugates described herein can be any protein or polypeptide molecule that can elicit an immune reaction (e.g., antibody production) when administered to a subject. Non-limiting examples of such immune reaction-stimulating polypeptides include, e.g., KLH, *Concholepas concholepas* hemocyanin (CCH), bovine serum albumin (BSA), cationized BSA, ovalbumin, an influenza hemagglutinin protein, and the like. Such immunogenic proteins are well known in the art.

Another aspect of the invention is the use of the immunogenic peptide conjugates described herein in a method of treating or preventing an influenza infection. The method comprises administering the peptide conjugate (e.g., in a therapeutically effective dose) to a subject. The peptide conjugates stimulate the immune system of the subject to produce a therapeutic antibody that specifically targets the FIR peptide portion of the conjugate. This therapeutic antibody response occurs despite the fact that the FIR peptide alone (without the carrier protein) does not elicit any immune response when administered to a subject. The immunogenic peptide conjugates can be included in a pharmaceutical composition in combination with a pharmaceutically acceptable carrier, if desired.

Another aspect of the present invention is an isolated therapeutic antibody capable of inhibiting fusion of a cell-bound influenza virus with the membrane of the cell to which the virus is bound. Preferably, the therapeutic antibody is a human, humanized, or chimeric monoclonal antibody. Such therapeutic antibodies can be obtained, for example, by isolating the antibody from sera of patients treated with an immunogenic peptide conjugate as described herein, creating a recombinant version of a human antibody from human subjects that have been treated with (i.e., administered) the immunogenic peptide conjugate, or by creating a recombinant chimeric or humanized version of an antibody from a suitable non-human host animal (e.g., a rabbit or goat) that has been treated with (i.e., administered) the immunogenic peptide conjugate.

The following non-limiting embodiments are provided to illustrate certain aspects and features of the present invention.

Embodiment 1 comprises an immunogenic peptide conjugate comprising a hemagglutinin fusion initiation region (FIR) peptide or a variant thereof, conjugated to an immunogenic carrier protein by a linking group. The hemagglutinin FIR peptide has an amino acid sequence that consists of SEQ ID NO: 1 or a variant of SEQ ID NO: 1 sharing at least 50% sequence identity therewith and differing from SEQ ID NO: 1 by one or more amino acid substitutions selected from the group consisting of V1I, V1L, V1A, V1G, V1T, V1S, V1M, E2D, E2K, E2R, D3E, T4G, T4S, T4Q, T4A, K5F, K5M, K5I, K5V, K5L, K5A, I6L, I6V, I6A, I6T, I6S, I6Q, I6N, D7E, L8I, L8V, L8A, W9Y, S10T, S10G, S10A, S10M, A13T, and E14K.

Embodiment 2 comprises the peptide conjugate of embodiment 1 wherein the immunogenic carrier protein is selected from the group consisting of the outer membrane protein complex of *Neiserria meningitidis* (OMPC), tetanus toxoid protein, diphtheria toxin derivative $CRM_{197}$, bovine serum albumin (BSA), cationized BSA, *Concholepas concholepas* hemocyanin (CCH), hepatitis B virus (HBV) surface antigen protein (HBsAg), HBV core antigen protein, keyhole limpet hemocyanin (KLH), a rotavirus capsid protein, bovine pappiloma virus (BPV) L1 protein, a human papilloma virus (HPV) L1 protein, ovalbumin, and a full-length influenza hemagglutinin (HA) protein.

Embodiment 3 comprises the peptide conjugate of embodiment 1 or embodiment 2 wherein the immunogenic carrier protein is a full-length influenza hemagglutinin protein.

Embodiment 4 comprises the peptide conjugate of embodiment 3 wherein the full-length influenza hemagglutinin protein is an influenza A hemagglutinin of a subtype, such as for example, a hemagglutinin selected from the group consisting of H1, H2, H3, H4, H5, H6, H7, H8, H9, H10, H11, H12, H13, H14, H15, H16 and H17.

Embodiment 5 comprises the peptide conjugate of embodiment 3 wherein the full-length influenza hemagglutinin protein is an influenza B hemagglutinin protein.

Embodiment 6 comprises the peptide conjugate of any one of embodiments 1 to 5 wherein the linking group comprises a sulfide bond (e.g., as in the case of common Cys to maleimide-type conjugation techniques described herein).

Embodiment 7 comprises the peptide conjugate of any one of embodiments 1 to 6 wherein the linking group is a 4-(N-succinimidomethylcyclohexane-1-carbonyl group of Formula I:

(I)

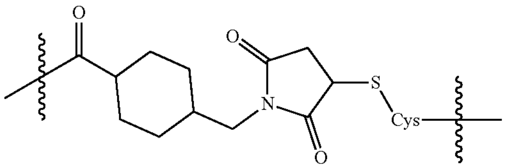

wherein the Cys residue of Formula I is bound to the succinimido moiety through the sulfhydryl group thereof and is bound the N-terminus of the FIR peptide by a peptide bond, optionally with an additional spacer peptide of 1 to 5 residues between the Cys and the FIR peptide, and the 1-carbonyl group on the cyclohexyl moiety of Formula I is bound to an primary amine on the carrier protein by an amide bond.

Embodiment 8 comprises the peptide conjugate of any one of embodiments 1 to 7 wherein the hemagglutinin FIR peptide has the amino acid sequence consisting of SEQ ID NO: 1.

Embodiment 9 comprises a pharmaceutical composition for treating or preventing an influenza infection comprising the immunogenic peptide conjugate of any one of embodiments 1 to 8 in a pharmaceutically acceptable carrier.

Embodiment 10 comprises a method of treating or preventing an influenza infection comprising administering a therapeutically effective amount of the immunogenic peptide conjugate of any one of embodiments 1 to 8 to a subject.

Embodiment 11 comprises a method of inducing a specific therapeutic antibody response in a subject comprising administering the immunogenic peptide conjugate of any one of embodiments 1 to 8 to a subject.

Embodiment 12 comprises the method of embodiment 11 wherein the specific therapeutic antibody response is inhibiting fusion of an influenza virus envelope with the membrane of a host cell.

Embodiment 13 comprises a therapeutic monoclonal antibody capable of specifically binding to the FIR region of an influenza virus hemagglutinin protein, the monoclonal antibody comprising complementarity determining regions (CDRs) from an antibody that specifically binds to the FIR region of an influenza virus hemagglutinin protein produced in a subject after being administered the immunogenic peptide conjugate of any one of embodiments 1 to 8.

Embodiment 14 comprises the therapeutic monoclonal antibody of embodiment 13 wherein the therapeutic monoclonal antibody is a human, humanized, or chimeric monoclonal antibody.

Embodiment 15 comprises use of the immunogenic peptide conjugate of any one of embodiments 1 to 8 for treating or preventing an influenza infection.

Embodiment 16 comprises use of the immunogenic peptide conjugate of any one of embodiments 1 to 8 for inducing a specific therapeutic antibody response against an influenza virus in a subject.

Embodiment 17 comprises the use of embodiment 16 wherein the specific therapeutic antibody response is inhibiting fusion of an influenza virus envelope with the membrane of a host cell.

Embodiment 18 comprises use of the immunogenic peptide conjugate of any one of embodiments 1 to 8 for the preparation of a medicament for treating or preventing an influenza infection.

Embodiment 19 comprises use of the therapeutic monoclonal antibody of embodiment 13 or embodiment 14 for treating or preventing an influenza infection.

Embodiment 20 comprises use of the therapeutic monoclonal antibody of embodiment 13 or embodiment 14 for the preparation of a medicament for treating or preventing an influenza infection.

A hemagglutinin FIR peptide that has the amino acid sequence consisting of VEDTKIDLWSYNAELL, SEQ ID NO: 1, has been found to have potent anti-viral properties (see U.S. Pat. No. 8,222,204). An immunogenic peptide conjugate comprising this same hemagglutinin FIR peptide conjugated to KLH elicited production of an antibody in mice, rabbits and goats that specifically targets the hemagglutinin FIR peptide. Surprisingly, this antibody was found to interfere with the virus envelope-to-host cell membrane fusion process, but did not significantly interfere with hemagglutination in a standard assay. This is in contrast to the mode of action of typical anti-influenza antibodies, which interfere with the actual physical interaction (e.g., binding) of the virus with the host cell.

BRIEF DESCRIPTION OF THE DRAWINGS

FIG. 2 provides a graph of results from a peptide binding competition assay comparing free FIR peptide versus ELISA plate-bound FIR peptide.

FIG. 3 provides a graph of binding competition between ELISA plate-bound hemagglutinin and free FIR peptide

DETAILED DESCRIPTION OF THE PREFERRED EMBODIMENTS

Figure 1:
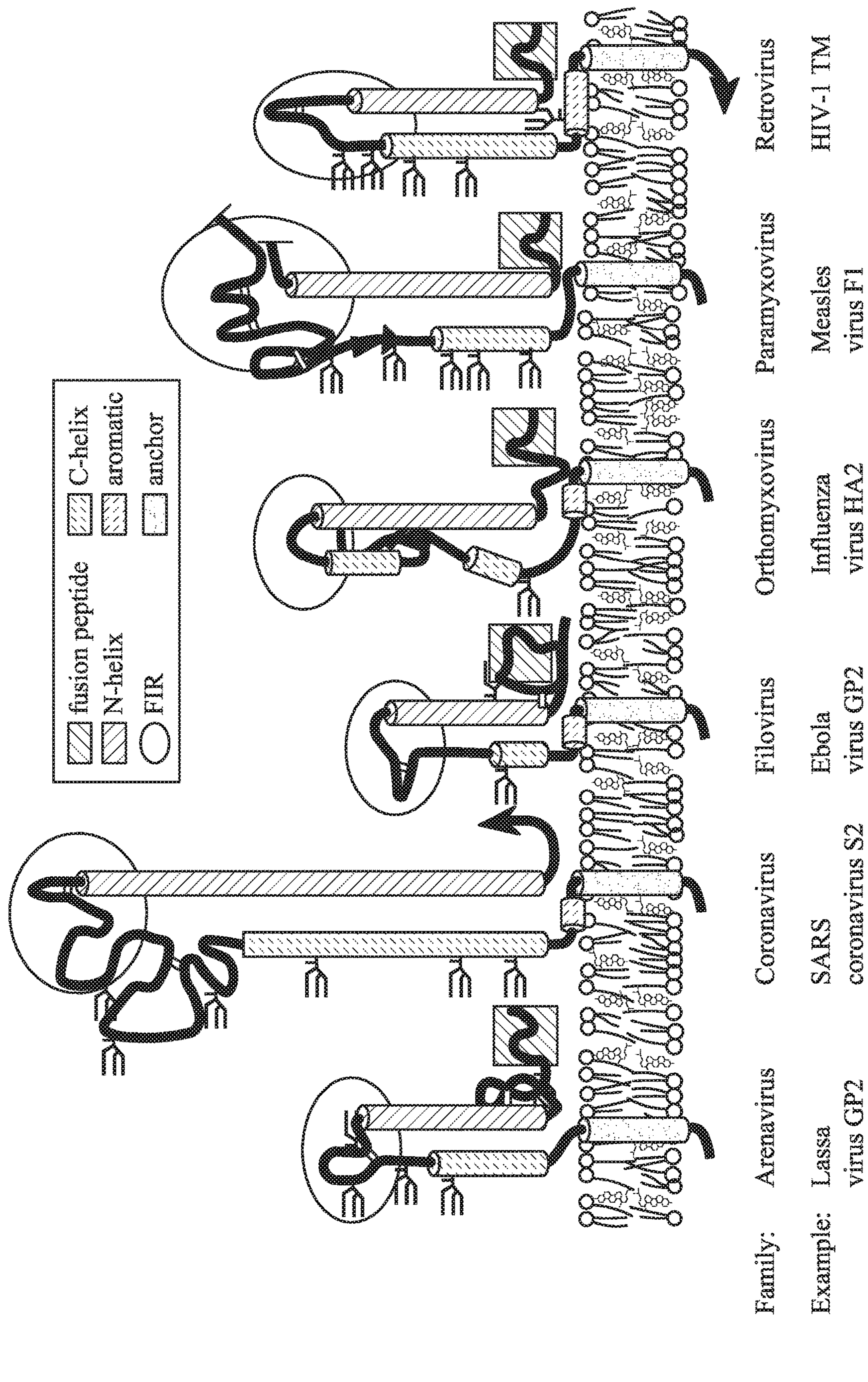
FIG. 1 shows the six identified domains of the fusion proteins from the six families of Type I viruses, including the fusion initiation region (FIR).

Immunogenic influenza hemagglutinin-derived peptide conjugates described herein induce a specific therapeutic antibody response against influenza virus. The immunogenic peptide conjugates are composed of a segment from the fusion initiation region (FIR) domain of an influenza hemagglutinin protein (referred to herein as the "hemagglutinin FIR peptide" or the "FIR peptide") conjugated to an immunogenic carrier protein. The hemagglutinin FIR peptide has an amino acid sequence that consists of SEQ ID NO: 1 or a variant of SEQ ID NO: 1 sharing at least 50% sequence identity therewith and differing from SEQ ID NO: 1 by one or more amino acid substitutions selected from the group consisting of V1I, V1L, V1A, V1G, V1T, V1S, V1M, E2D, E2K, E2R, D3E, T4G, T4S, T4Q, T4A, K5F, K5M, K5I, K5V, K5L, K5A, I6L, I6V, I6A, I6T, I6S, I6Q, I6N, D7E, L8I, L8V, L8A, W9Y, S10T, S10G, S10A, S10M, A13T, and E14K.

SEQ ID NO: 1 is a segment (i.e., residues 84 to 99) of the FIR of an influenza A hemagglutinin, subtype H3 strain, which has the amino acid sequence of SEQ ID NO: 2. FIR peptides that are variants of SEQ ID NO: 1 differ therefrom by specific substitutions that are either conservative substitutions or are substitutions of corresponding amino acid residues from another hemagglutinin subtype (i.e., from H1, H2, H4, H5, H6, H7, H9, H10, H11, H12, H13, H15, H16 or H17). Peptides corresponding to SEQ ID NO: 1 from these other subtypes are shown in Table 1. Preferably the variant is identical to or shares a high sequence identity (e.g., 95% or greater sequence identity, preferably 98% or greater sequence identity, more preferably 100% sequence identity) with SEQ ID NO: 1.

As used herein, the term "conservative substitutions" and grammatical variations thereof, refers to the presence of an amino acid residue in the sequence of a peptide that is different from, but is in the same class of amino acid as the wild-type residue (i.e., a nonpolar residue replacing a nonpolar residue, an aromatic residue replacing an aromatic residue, a polar-uncharged residue replacing a polar uncharged residue, a charged residue replacing a charged residue). In addition, conservative substitutions can encompass a residue having an interfacial hydropathy value of the same sign and generally of similar magnitude as the wild-type residue that it replaces.

As used herein, the term "nonpolar residue" refers to glycine, alanine, valine, leucine, isoleucine, and proline; the term "aromatic residue" refers to phenylalanine, tyrosine, tryptophan and histidine (which also is considered a charged amino acid); the term "polar uncharged residue" refers to serine, threonine, cysteine, methionine, asparagine and glutamine; the term "charged residue" refers to the negatively charged amino acids aspartic acid and glutamic acid, as well as the positively charged amino acids lysine, arginine, and histidine (which also is considered an aromatic amino acid).

TABLE 1

| Peptide Sequence | Sequence ID | Hemagglutinin A Subtype |
|---|---|---|
| VEDTKIDLWSYNAELL | SEQ ID NO: 1 | H3, H4 and H14 |
| VDDGFLDIWTYNAELL | SEQ ID NO: 3 | H1 |
| MEDGFLDVWTYNAELL | SEQ ID NO: 4 | H5 |
| TRDSMTEVWSYNAELL | SEQ ID NO: 5 | H7 |
| VDDQIQDIWAYNAELL | SEQ ID NO: 6 | H9 |
| MEDGFLDVWTYNAELL | SEQ ID NO: 7 | H2 and H6 |
| TKDSITDIWTYNAELL | SEQ ID NO: 8 | H10 |

TABLE 1-continued

| Peptide Sequence | Sequence ID | Hemagglutinin A Subtype |
|---|---|---|
| IDDAVTDIWSYNAKLL | SEQ ID NO: 9 | H13 |
| TRDSLTEIWSYNAELL | SEQ ID NO: 10 | H15 |
| VDDAVTDIWSYNAKLL | SEQ ID NO: 11 | H16 |
| VDDALLDIWSYNTELL | SEQ ID NO: 12 | H17 |

All of the sequences in Table 1 share greater than 50 percent sequence identity with SEQ ID NO: 1, i.e., SEQ ID NO: 3, 4, 6, 7, and 12 are 62.5 percent identical to SEQ ID NO: 1; and SEQ ID NO: 5, 8, 9, 10 and 11 are 56.2 percent identical to SEQ ID NO: 1. Thus, it is clear that the various influenza hemagglutinin subtypes are highly homologous in the 16-amino acid residue segment of the FIR exemplified by SEQ ID NO: 1. The substitutions in the FIR peptide portion (SEQ ID NO: 1) of the immunogenic peptide conjugates described herein are derived primarily from the variations found in SEQ ID NO: 3 through 12 shown in Table 1, as well as common conservative substitutions for one of the residues found in SEQ ID NO: 1 and 3 through 12, such as substitutions of a valine residue by a leucine, glycine, serine, or alanine; substitution of an aspartic acid residue with a glutamic acid residue; substitution of a serine residue by a glycine or methionine; and the like.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Immunogenic carrier proteins useful in the peptide conjugates and methods described herein include any immunogenic protein that can elicit antibody production when administered to a subject. Such carrier proteins and methods of conjugating the carrier proteins to a peptide of interest are well known in the art and have been used in the production of so-called "conjugate vaccines". Some examples of carrier proteins, linking groups, and conjugation methods are described in PCT International Publication No. WO2012/065034, filed as Application No. PCT/US2011/060318, which is incorporated herein by reference in its entirety. Some non-limiting examples of carrier proteins include the outer membrane protein complex of *Neiserria meningitidis* (OMPC), tetanus toxoid protein, a derivative of diphtheria toxin (CRM197), bovine serum albumin (BSA), cationized-BSA, *Concholepas concholepas* hemocyanin (CCH), hepatitis B virus (HBV) proteins (e.g., the surface antigen protein (HBsAg), and the HBV core antigen protein), keyhole limpet hemocyanin (KLH), rotavirus capsid proteins, the L1 protein of a bovine pappiloma virus (BPV L1), the L1 protein of human papilloma virus (HPV L1; e.g., HPV type 6, 11 or 16), ovalbumin, and influenza hemagglutinin (HA) proteins, such as HA proteins from hemagglutinin A subtypes H1 to H17. Representative sequences of influenza HA proteins include H1 (SEQ ID NO: 13), H2 (SEQ ID NO: 14), H3 (SEQ ID NO: 15), H5 (SEQ ID NO: 16), and H7 (SEQ ID NO: 17). The choice of carrier protein, coupling (conjugation) technique and linking group for use in the immunogenic peptide conjugates described herein is well within the ability of a person of ordinary skill in the protein vaccine synthesis art.

Carrier proteins are conjugated via reactive sites on the carrier proteins and peptides of interest via a linking group. Nucleophilic functional groups useful for conjugation are well known in the art (see e.g., U.S. Pat. No. 5,606,030, which is incorporated herein by reference in its entirety). For example, primary amino groups present on amino acid residue such as the epsilon amino group of lysine, and the alpha amino group of N-terminal amino acids of proteins can be used as functional groups for conjugation. Often it is desirable to convert one or more primary amino groups of a carrier protein to a thiol-containing group (e.g., from a cysteine or homocysteine residue), an electrophilic unsaturated group such as a maleimide group, or halogenated group such as a bromoacetyl group, for conjugation to thiol reactive peptides. Optionally, a primary amino group on the hemagglutinin FIR peptide or on a linker moiety attached to the peptide, can be converted to the thiol-containing group, for coupling with a thiol (sulfhydryl) moiety on the carrier protein, e.g., by a disulfide bond.

The hemagglutinin FIR peptides and the carrier proteins can be conjugated using any linking groups and conjugation methods known in the art. In some embodiments, the conjugation can be achieved, for example, by using succinimidyl 4-[N-maleimidomethyl]cyclohexane-1-carboxylate (SMCC), sulfosuccinimidyl 4-(N-maleimidomethyl)cyclohexane-1-carboxylate (sSMCC), ε-[ε-maleimidocaproyloxy]-sulfosuccinimde ester (sEMCS), bis-diazobenzidine (BDB), N-maleimidobenzoyl-N-hydroxysuccinimide ester (MBS), glutaraldehyde, 1-ethyl-3-(3-dimethylaminopropyl) carbodiimide (EDCI), or N-acetyl homocysteine thiolactone (NAHT).

In the SMCC method, SMCC cross-links the SH-group of a cysteine residue to the amino group of a lysine residue on the carrier protein. In the SMCC method, the carrier protein first is activated by reacting SMCC with a primary amine (e.g., on a lysine residue of the carrier protein). The resulting activated carrier is then separated from any excess SMCC and by-product therefrom, and a cysteine-containing peptide is added. The thiol group of the cysteine adds across the double bond of the maleimide moiety of the SMCC-derivatized carrier protein, thus forming a covalent sulfide bond to couple the carrier to the peptide. If a hemagglutinin FIR peptide does not include a cysteine residue, then a cysteine residue should be added to the peptide, preferably at the N-terminus or C-terminus. If the epitope portion of the hemagglutinin FIR peptide contains a cysteine or if there is more than one cysteine group in the peptide, then another conjugation technique that does not modify the cysteine residues should be utilized. Since the linkage between the carrier protein and the peptide should not interfere with the epitope portion of the peptide, the added cysteine residue optionally can be separated from the hemagglutinin FIR peptide by including one or more amino acid residues as a spacer. The cysteine, spacer residues, and the modified SMCC attached to the carrier together constitute the linking group of the hemagglutinin FIR peptide conjugate.

Another simple coupling of a peptide to a carrier protein can be achieved with a carbodiimide crosslinker such as 1-ethyl-3-(3-dimethylaminopropyl) carbodiimide hydrochloride (EDC), 1-cyclohexyl-2-(2-morpholinoethyl) carbodiimide metho-p-toluenesulfonate (CMC), and the like to covalently attach carboxyl groups to primary amine groups. This method is simple and provides a relatively random orientation that allows for antibody generation against many possible epitopes. One drawback is that EDC coupling can result in some amount of polymerization. This can decrease the solubility of the conjugate, which can complicate the handling of the material.

Other coupling agents can be used to conjugate the FIR peptide to the carrier protein, either directly or via a linking group. For example, conjugation can be achieved using isocyanate coupling agents, such as 2-morpholinoethylisocyanide; N-acetyl homocysteine thiolactone, which can be used to add a thiol group onto a carrier protein such as OMPC coupling with a maleimide or bromoacetyl functionalized peptide; or any other agents for coupling haptens (potential immunogens) to polypeptides and proteins, many of which are well known in the protein and vaccine arts.

Non-specific cross-linking agents and their use are well known in the art. Examples of such reagents and their use include reaction with glutaraldehyde; reaction with N-ethyl-N'-(3-dimethylaminopropyl)carbodiimide, with or without admixture of a succinylated carrier; periodate oxidation of glycosylated substituents followed by coupling to free amino groups of a protein carrier in the presence of sodium borohydride or sodium cyanoborohydride; periodate oxidation of non-acylated terminal serine and threonine residues forming terminal aldehydes which can then be reacted with amines or hydrazides creating a Schiff base or a hydrazone, which can be reduced with cyanoborohydride to secondary amines; diazotization of aromatic amino groups followed by coupling on tyrosine side chain residues of the protein; reaction with isocyanates; or reaction of mixed anhydrides. The linkers can be supplemented and extended with spacer groups, such as additional amino acid residues, adipic acid dihydrazide, and the like.

Typical spacer peptide groups for use in conjugation of the FIR peptide to the carrier protein include single amino acids (e.g., Cys) and short peptide sequences (i.e., short non-hemagglutinin FIR peptide sequences) attached to the FIR peptide, e.g., a lysine containing peptide such as the flag tag sequence DYKDDDDK (SEQ ID NO: 18), a cysteine-containing peptide, and the like. Some preferred linking groups comprise a sulfide bond (e.g., as in SMCC and related coupling methods). Some preferred linking groups includes 4-(N-succinimidomethylcyclohexane-1-carbonyl groups of Formula I:

(I)

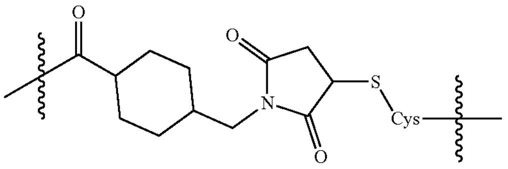

in which the Cys residue in Formula I is bound to the succinimido moiety through the sulfhydryl side chain thereof and is bound the N-terminus of the FIR peptide by a peptide bond. Optionally an additional spacer peptide of 1 to 5 amino acid residues can be included between the Cys and the FIR peptide. The 1-carbonyl group on the cyclohexyl moiety of Formula I is bound to a primary amine on the carrier protein by an amide bond.

In some embodiments, the peptide conjugates include a single hemagglutinin FIR peptide attached to the carrier protein, while in other embodiments, two or more hemagglutinin FIR peptides can be attached to the carrier protein.

In another aspect, the present invention provides a therapeutic monoclonal antibody that is specific for (i.e., is capable of specifically and selectively binding to) the hemagglutinin FIR peptide portion of the immunogenic peptide conjugates described herein and of binding to the FIR of the HA2 of an influenza virus. Such therapeutic monoclonal antibodies comprise complementarity determining regions (CDRs) derived from an antibody that specifically binds to the FIR portion of an immunogenic peptide conjugate as described herein. The therapeutic antibodies can be human antibodies (e.g., isolated from the serum of a subject exposed to the peptide conjugate), a non-human antibody (e.g., isolated from a non-human subject organism such as a mouse, rat, rabbit, goat or other suitable organism exposed to the peptide conjugate), as well as chimeric and humanized versions of such nonhuman antibodies.

When administered (e.g., in a therapeutically effective dose) to a subject exposed to an influenza virus, the therapeutic monoclonal antibodies inhibit influenza virus-to-host cell membrane fusion and thus prevent infection of the host cell by the influenza virus. This inhibition is achieved by binding of the antibody to the FIR region of the HA protein of an influenza virus. Thus, the therapeutic monoclonal antibodies described herein have a therapeutic mechanism that is the same as or very similar to the hemagglutinin FIR peptide portion of the immunogenic peptide conjugate (see U.S. Pat. No. 8,222,204 for a discussion of the therapeutic mechanism of the FIR peptides).

As used herein, the term "therapeutically effective dosage" and grammatical variations thereof, refers to an amount of an immunogenic peptide conjugate such that when administered to a subject elicits a specific therapeutic antibody response against an influenza virus, or an amount of a therapeutic antibody sufficient to prevent or provide a clinical reduction in an influenza infection. The dosage and number of doses (e.g. single or multiple dose) administered to a subject will vary depending upon a variety of factors, including the route of administration, patient conditions and characteristics (sex, age, body weight, health, size), extent of symptoms, concurrent treatments, frequency of treatment and the effect desired, the concentration of the conjugate or antibody in the administered form thereof, and the like. Adjustment and manipulation of dosage ranges, as well as in vitro and in vivo methods of determining the therapeutic effectiveness of the composition in an individual, are well within the ability of those of ordinary skill in the medical arts. By way of example, a dose in the range of about 1 to 100 mL of a solution comprising the peptide conjugate or therapeutic antibody in a pharmaceutically acceptable carrier may be utilized. The peptide conjugate or the therapeutic antibody would be present in the solution at a concentration in the range of about 0.01 μg/mL to about 10 mg/mL. The peptide or antibody can be administered parenterally (e.g., by intravenous, intraperitoneal, subcutaneous, or intramuscular injection or infusion) or transmucosally (e.g., by inhalation of an aerosolized liquid or powder composition).

The binding specificity and the mechanism by which the therapeutic antibodies described herein operate is in distinct contrast to antibodies formed in response to vaccination with traditional influenza vaccines, which typically interfere with the physical interaction of the virus with a host cell and are usually strain specific, as underscored by the necessity of yearly reformulation of the seasonal vaccine to match the circulating strains of influenza. In contrast, the therapeutic antibodies described herein surprisingly interfere with the viral fusion process and are broadly reactive against different strains of influenza (including both influenza A and B).

Preferably, the therapeutic monoclonal antibody is a human, humanized, or chimeric monoclonal antibody. Methods for preparing monoclonal antibodies are well known in the art, as are commercial enterprises that routinely create monoclonal antibodies from isolated natural antibodies. Chimeric and humanized monoclonal antibodies and methods of producing such antibodies also are well known in the antibody art (see e.g., U.S. Pat. Nos. 5,824,307; 6,800,738; 7,070,775; 7,087,409; 7,456,260; and 7,807,161; each of which is incorporated herein by reference in its entirety).

The chimerization process involves replacing portions of a nonhuman antibody with corresponding portions from a human antibody (e.g., a constant region). This is done to prevent the human immune system from attacking the nonhuman antibody as a foreign proteins. The chimeric antibody generally retains the CDRs and or the entire variable region of the nonhuman antibody and replaces the nonhuman constant domains with human constant domains. Thus, the chimeric antibody retains the antigen specificity of the nonhuman antibody, but has a reduced level of undesirable immune reactions (e.g., allergic reactions) against the antibody.

Humanized antibodies are similar to chimeric antibodies, except that humanized antibodies generally include fewer non-human features. This can be achieved e.g., by modifying the sequence of the variable region of a chimeric antibody to better reflect the characteristics of a human antibody, e.g., by modifying the sequences between the CDRs or other portions of the nonhuman sequences in the antibody. Not all of the therapeutic monoclonal antibodies may need to be humanized, since some therapeutic treatments may be of a short enough duration to make allergic side effects less likely.

Fully human antibodies also can be utilized. Such human antibodies can be, for example, genetically engineered antibodies, e.g., antibodies in which the CDRs are of human origin, but which have human-derived structures that differ in one or more aspects from a naturally produced human antibody (i.e., an antibody produced by a human subject treated with the immunogenic peptide conjugate); or the human antibodies can be clones of natural antibodies obtained from the serum of a human subject treated with the peptide conjugate.

In another aspect, pharmaceutical compositions are provided, which comprise an immunogenic peptide conjugate or antibody as described herein, and which can be used for treating or preventing an influenza infection. In certain preferred embodiments, this composition includes the immunogenic peptide conjugate or antibody in a pharmaceutically acceptable vehicle or carrier suitable for delivery of the peptide, analog, derivative or antibody to a subject, e.g., by parenteral or enteral administration, preferably by injection (e.g., preferably by intravenous, intraperitoneal, subcutaneous, or intramuscular injection), or by nasal (e.g., aerosol) administration. Vehicles and carriers suitable for delivering an active ingredient are well known in the art and include saline solutions, buffered saline solutions, and the like, preferably at physiological pH (e.g., a pH of about 6.5 to 7.4). The carrier can also include other excipient ingredients, such as surfactants, preservatives, dispersants, diluents, stabilizers, and the like, which are well known in the pharmaceutical formulation art. The pharmaceutical composition can be used as part of a method to treat or prevent an influenza infection by administering to a subject a therapeutically effective amount of the pharmaceutical composition. The carriers for the peptide conjugates and antibodies can be solids or liquids, the choice of which is determined by the desired mode of administration.

The following non-limiting examples are provided to further illustrate certain aspects and features of the immunogenic peptide conjugates and methods described herein.

Example 1. Preparation of a Hemagglutinin FIR Peptide-KLH Conjugate

The FIR peptide of SEQ ID NO: 1 was synthesized with an added N-terminal Cys linking residue; i.e., to produce the peptide of SEQ ID NO: 19, which was then conjugated with KLH using the SMCC method. Briefly, the carrier KLH protein first was activated by reacting SMCC with one or more primary amine groups (e.g., on a lysine residue of the carrier protein). The resulting activated carrier was then separated from any excess SMCC and by-product therefrom. The cysteine-derivatized FIR peptide then was reacted with activated KLH; the sulfhydryl (thiol) group of the cysteine adding across the double bond of the maleimide moiety of the SMCC-derivatized carrier protein, thus forming a covalent sulfide bond. The resulting FIR peptide-KLH conjugate was then isolated.

Example 2. Production of Mouse Monoclonal Anti-FIR Peptide Antibody

Five Balb/C mice were injected with the conjugate as prepared in Example 1. The first injection utilized the FIR peptide-KLH conjugate mixed with complete Freund's adjuvant on day 0. On days 21, 35, 49, and 63 the mice were injected with the FIR-peptide-KLH conjugate in incomplete Freund's adjuvant. Serum samples were collected from the mice on days 45, 59, and 73, and tested for the presence of anti-FIR peptide antibodies using an ELISA method with the FIR peptide (SEQ ID NO: 1) passively bound to the wells of 96-well plastic plates. Three mice with the highest titer of anti-FIR antibodies were sacrificed and the spleens were harvested. Using standard techniques, splenocytes were harvested and fused with sp2/0 cells, and hybridomas producing anti-FIR antibodies were identified by ELISA and subcloned by limiting dilution. Several clones were identified and one designated MAF3-2, was used in further analysis.

Example 3. Production of Therapeutic Anti-FIR Peptide Antibody in Goats

A goat was injected with the conjugate as prepared in Example 1. The first injection was with 500 μg of the FIR peptide-KLH conjugate in complete Freund's adjuvant. Subsequent injections, at two-week intervals, were with 250 μg doses of the conjugate in incomplete Freund's adjuvant. After a total of three injections, a serum sample was prepared at week 5 after the first injection. The serum sample was found to contain a detectable titer to the FIR peptide in a plate ELISA test.

The goat was injected once more with 250 μg of the FIR peptide-KLH and sera samples were prepared at weeks 7 and 8. The serum samples from weeks 7 and 8 were titrated for their reactivity to the FIR peptide (SEQ ID NO: 1) with a plate ELISA assay. The plates were coated with non-conjugated FIR peptide and antibodies in the serum samples were found to specifically bind to the coated plate.

Example 4. Production of Therapeutic Anti-FIR Peptide Antibody Rabbits

Two rabbits were injected with the conjugate as prepared in Example 1. The first injection was with 200 μg of the FIR peptide-KLH conjugate in complete Freund's adjuvant. Subsequent injections, at two-week intervals, were with 100 μg doses of the conjugate in incomplete Freund's adjuvant. After a total of three injections, serum samples were drawn from each animal at week 5 after the first injection. The serum samples were found to contain a detectable titer to the FIR peptide in a plate ELISA test.

The rabbits were injected once more and serum samples were collected at weeks 7 and 8. The serum samples from weeks 7 and 8 were titrated for their reactivity to the FIR peptide with a plate ELISA assay. The plates were coated with non-conjugated FIR peptide by standard methods and the sera samples were found to specifically bind to the coated plate. An antibody was isolated from a serum sample by binding to FIR peptide attached to a solid chromatography support. The antibody was released by low pH (i.e., about pH 2.68).

The isolated antibody was found to be specific for the FIR peptide, as commonly defined by competition between plate-bound FIR peptide and free FIR peptide in solution. To demonstrate specificity, 96-well immunoassay plate wells were coated with the FIR peptide dissolved in carbonate-bicarbonate buffer. Nonbound charged sites on the plastic were blocked with a buffered nonfat dry milk/detergent suspension. The purified rabbit anti-FIR peptide antibody was coupled to biotin. About 0.1 mL aliquots of the biotinylated antibody solution were then neutralized by serial dilutions of FIR peptide for about 45 minutes before adding to the plate. After further incubation, the wells were washed with buffered saline containing detergent. The bound anti-FIR antibody was detected by incubation with a streptavidin-horseradish peroxidase conjugate followed by washing and application of a colorimetric reagent, 3,3',5,5'-tetramethylbenzidine. FIG. 2 provides a graph of binding competition between plate-bound and free FIR peptide.

Example 5. Broad Spectrum Binding by a Mouse Monoclonal Antibody

An isolated mouse-sourced monoclonal antibody to FIR peptide from Example 2 (MAF3-2) was found to recognize and specifically bind to various subtypes of hemagglutinin (HA) as commonly defined by competition with FIR peptide antigen. To demonstrate specificity, 96-well immunoassay plate wells were coated with various subtypes of commercially available hemagglutinin (HA: H1 strain A/California/04/2009 (H1N1) pdm09; H3 strain A/Uruguay/716/07 (H3N2); H3 strain A/Wisconsin/67/2005 (H3N2); H5 strain A/bar-headed goose/Qinghai/1A/05 (H5N1)) dissolved in carbonate-bicarbonate buffer. Nonbound charged sites on the plastic were blocked with a buffered nonfat dry milk/detergent suspension. The purified MAF3-2 antibody was coupled to biotin (btn-MAF3-2). About 0.1 mL aliquots of the antibody solution were then neutralized by serial dilutions of FIR peptide for about 45 minutes before adding to the HA coated plate. After further incubation, the wells were washed with buffered saline containing detergent. The bound FIR antibody was detected by incubation with a streptavidin-horseradish peroxidase conjugate followed by washing and application of a colorimetric reagent, 3,3',5,5'-tetramethylbenzidine. FIG. 3 provides a graph of binding competition between ELISA plate-bound HA and free FIR peptide, which again demonstrates specificity of the anti-FIR peptide antibody for the FIR antigen.

Example 6. Evaluation of Therapeutic Anti-FIR Peptide Antibody Against Influenza Viruses Cells and Viruses: Madin Darby Canine Kidney cells (MDCK) were used for all experiments. Cells were maintained and propagated in complete Dulbecco's Minimum Essential Medium (cDMEM) supplemented with penicillin/streptomycin solution, sodium bicarbonate solution, non-essential amino acids solution, and heat inactivated fetal bovine serum. Influenza viruses included in Table 2 were used for all infection/antibody binding studies. All viruses were propagated in 9-day old embryonated chicken eggs using standard methods and purified by centrifugation from allantoic fluids. All infections were performed at a multiplicity of infection of 5.0.

TABLE 2

Influenza A and B viruses utilized in FIR antibody binding studies.

| Virus | Subtype | Description and Comments |
|---|---|---|
| A/California/04/2004 | H3N2 | Seasonal |
| A/Hong Kong/2369/2009 | H1N1 | Pandemic, oseltamivir phosphate resistant |
| A/PR/8/1934-H5N1 | H5N1 | Reassortant virus containing H5N1 from A/Vietnam/1203/2004 |
| B/Shanghai/362/2002 | B | Seasonal |

Antibodies and reagents: The goat anti-FIR peptide antibody serum from Example 3 was maintained at 4° C. until used in binding studies. Binding studies were performed with antibody diluted 1:500 in phosphate buffered saline (PBS) supplemented with 1% bovine serum albumin. As a control for influenza A or B infection, staining of duplicate cultures was performed using mouse monoclonal antibody raised against the influenza A or influenza B nucleoprotein (NP) (Santa Cruz Biotechnology) at 1:1000 dilution in PBS/BSA. Secondary antibodies (anti-goat or anti-mouse) conjugated to horseradish peroxidase (HRP) or ALEXA 488 (Molecular Probes) were used for visualization of bound primary antibody.

MDCK infection and antibody binding protocol: MDCK cells were grown to 90% confluence in chamber slides using standard methods. For virus infection, media were removed and each virus was added to the appropriate chamber in a volume of 200 μL for one hour at 37° C. in a humidified $CO_2$ incubator. After incubation, unbound virus was removed by aspiration with washing, and media replaced with serum-free cDMEM supplemented with TPCK trypsin (Worthington Chemicals, USA). Infected MDCK cells were incubated at 35° C./5% $CO_2$ for 24 hours to allow virus replication. For antibody binding studies, media were removed from each chamber and cells were fixed with 4% paraformaldehyde (in PBS) for 30 minutes at 4° C. After washing, cells were permeabilized and residual aldehydes blocked by incubation with PBS+20 mM glycine/0.01% TRITON X-100 surfactant at room temperature for twenty minutes. Following washing, goat anti-FIR serum (1:500 in PBS+1% BSA) was added to chambers for three hours at room temperature. Unbound antibody was removed with washing in PBS. Visualization of bound anti-FIR peptide was performed by incubation for 30 minutes with a secondary antibody (anti-goat) conjugated to either ALEXA 488 or horseradish peroxidase for fluorescent or visible detection microscopy. After removal of unbound secondary antibody by washing (PBS/BSA), HRP conjugate-treated chambers were developed by adding 3-amino-9-ethylcarbazole (AEC) substrate reagents (Vector labs USA) according to manufacturer's instructions. ALEXA 488 conjugated chambers were mounted using VECTASHIELD aqueous mounting media (Vector labs USA) supplemented with propidum iodide counterstain and slides were sealed with nail polish after addition of a coverslip.

Microscopic evaluation of antibody binding: Slide chambers were evaluated by visible light microscopy using an EVOS light microscope with digital image capture capability (AMG Instruments, USA). Representative images were captured using instrument software and saved as Tagged Image Files (TIF). Fluorescently labeled (ALEXA 488) stained chambers were examined using a Zeiss LSM 700 laser scanning confocal microscope (Jena Germany) using 488 nm and 455 nm laser lines to visualize green and red fluorescence respectively. LSM software was used to save representative images as Tagged Image Files (TIF).

Visible images were obtained for infected cells prior to fixing and antibody binding. Cytopathic effects of virus infection at 24 hours post infection were observed in A/Hong Kong/2369/2009, A/PR/8/34 (H5N1) and B/Shanghai/362/2002 infected MDCK cell cultures. Influenza A/California/04/2004 did not induce CPE at this time point post infection.

The visible (AEC) and fluorescent (Alexa488) staining images of the anti-FIR peptide antibody or anti-influenza nucleocapsid protein (NP) antibody (A or B) were evaluated visually. In all viruses examined, positive staining was observed with both NP and anti-FIR antibody with a range of reactivity observed. In both visualization conditions, more diffuse staining was observed with H5 expressing cells (A/PR/8/1934+H5N1) than with H1, H3, or influenza B infected cells. Table 3 provides a summary of the observed binding properties. The number of + symbols in Table 3 indicates the degree of binding of the antibody to the cells infected with the indicated viruses; a larger number of + symbols indicates a higher degree of binding.

TABLE 3

Antibody Binding Summary.

| Virus | Subtype | Description | FIR MAb | NP MAb |
|---|---|---|---|---|
| A/California/04/2004 | H3N2 | Seasonal | +++ | +++ |
| A/Hong Kong/2369/2009 | H1N1 | Pandemic, oseltamivir phosphate resistant | +++ | + |
| A/PR/8/1934-H5N1 | H5N1 | Reassortant virus containing H5N1 from A/Vietnam/1203/2004 | +++ | ++++ |
| B/Shanghai/362/2002 | B | Seasonal | + | ++ |

Taken together, these results indicate broad specificity of binding with regard to influenza A and B viruses for antibodies raised against the FIR peptide of SEQ ID NO: 1. This breadth may be due to the high homology of the hemagglutinin proteins of the various subtypes in the region from which the FIR peptide is derived. Binding of control antibody that recognizes influenza nucleoprotein (NP) confirmed MDCK cells were infected with each virus confirming the specificity of anti-FIR peptide antibody for influenza virus.

In summary, administering the peptide conjugate comprised of the hemagglutinin FIR peptide of SEQ ID NO: 1 conjugated with KLH to rabbits, mice, and goats stimulated the production of anti-FIR peptide antibodies by the animals. In tests with influenza A (H1, H3 and H5) and influenza B viruses, sera from these animals were surprisingly found to bind to the FIR peptide itself, to bind to cells exposed to virus, and to inhibit viral infectivity. The antibodies reacted with HA on the surface of exposed cells as detected using both visible and fluorescent techniques. Sera from subjects vaccinated with a recent influenza vaccine produce a robust anti-HA response, but surprisingly appeared not to produce antibodies against the FIR peptide of SEQ ID NO: 1.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. An immunogenic peptide composition comprising a hemagglutinin fusion initiation region (FIR) peptide or a variant thereof, bound to an immunogenic carrier protein; wherein the hemagglutinin FIR peptide has an amino acid sequence that consists of SEQ ID NO: 1 or a variant of SEQ ID NO: 1 sharing at least 50% sequence identity therewith and differing from SEQ ID NO: 1 by one or more amino acid substitutions selected from the group consisting of V1I, V1L, V1A, V1G, V1T, V1S, V1M, E2D, E2K, E2R, D3E, T4G, T4S, T4Q, T4A, K5F, K5M, K5I, K5V, K5L, K5A, I6L, I6V, I6A, I6T, I6S, I6Q, I6N, D7E, L8I, L8V, L8A, W9Y, S10T, S10G, S10A, S10M, and E14K; and wherein the immunogenic carrier protein is selected from the group consisting of the outer membrane protein complex of *Neisseria meningitidis* (OMPC), tetanus toxoid protein, diphtheria toxin derivative $CRM_{197}$, *Concholepas concholepas* hemocyanin (CCH), hepatitis B virus (HBV) surface antigen protein (HBsAg), HBV core antigen protein, a rotavirus capsid protein, bovine papilloma virus (BPV) L1 protein, a human papilloma virus (HPV) L1 protein, and ovalbumin.

2. An immunogenic peptide composition comprising a first influenza polypeptide bound to a second influenza polypeptide; wherein the first influenza polypeptide consists of 16 amino acid residues and has an amino acid sequence consisting of SEQ ID NO: 1 or a variant of SEQ ID NO: 1 sharing at least 50% sequence identity therewith and differing from SEQ ID NO: 1 by one or more amino acid substitutions selected from the group consisting of V1I, V1L, V1A, V1G, V1T, V1S, V1M, E2D, E2K, E2R, D3E, T4G, T4S, T4Q, T4A, K5F, K5M, K5I, K5V, K5L, K5A, I6L, I6V, I6A, I6T, I6S, I6Q, I6N, D7E, L8I, L8V, L8A, W9Y, S10T, S10G, S10A, S10M, and E14K; and the second polypeptide consists of a full-length influenza hemagglutinin protein; and wherein the first polypeptide is bound to the second polypeptide either directly or through a linking group comprising a spacer peptide selected from the group consisting of a single amino acid and a non-hemagglutinin FIR peptide sequence.

3. The composition of claim 2, wherein the full-length influenza hemagglutinin protein is a hemagglutinin from an influenza A subtype selected from the group consisting of H1, H2, H3, H4, H5, H6, H7, H8, H9, H10, H11, H12, H13, H14, H15, H16 and H17.

4. A pharmaceutical composition for treating or preventing an influenza infection comprising the immunogenic peptide composition of claim 1 in a pharmaceutically acceptable carrier.

5. A pharmaceutical composition for treating or preventing an influenza infection comprising the immunogenic peptide composition of claim 2 in a pharmaceutically acceptable carrier.

6. A method of treating an influenza infection comprising administering a therapeutically effective amount of the immunogenic peptide composition of claim 1 to a subject.

7. A method of treating an influenza infection comprising administering a therapeutically effective amount of the immunogenic peptide composition of claim 2 to a subject.

8. The method of claim 7, wherein the full-length influenza hemagglutinin protein is a hemagglutinin from an influenza A subtype selected from the group consisting of H1, H2, H3, H4, H5, H6, H7, H8, H9, H10, H11, H12, H13, H14, H15, H16 and H17.

9. A method of inhibiting fusion of an influenza virus with the membrane of a host cell in a subject comprising administering the immunogenic peptide composition of claim 1 to the subject.

10. A method of inhibiting fusion of an influenza virus with the membrane of a host cell in a subject comprising administering the immunogenic peptide composition of claim 2 to the subject.

11. The composition of claim 2, wherein the first polypeptide consists of SEQ ID NO: 1.

12. The composition of claim 2, wherein the first polypeptide consists of a variant of SEQ ID NO: 1 sharing at least 50% sequence identity therewith and differing from SEQ ID NO: 1 by one or more amino acid substitutions selected from the group consisting of V1I, V1L, V1A, V1G, V1T, V1S, V1M, E2D, E2K, E2R, D3E, T4G, T4S, T4Q, T4A, K5F, K5M, K5I, K5V, K5L, K5A, I6L, I6V, I6A, I6T, I6S, I6Q, I6N, D7E, L8I, L8V, L8A, W9Y, S10T, S10G, S10A, S10M, and E14K.

13. The composition of claim 12, wherein the variant has a sequence selected from the group consisting of SEQ ID NO: 3, SEQ ID NO: 4, SEQ ID NO: 5, SEQ ID NO: 6, SEQ ID NO: 8, SEQ ID NO: 9, SEQ ID NO: 10, and SEQ ID NO: 11.

14. The method of claim 7, wherein the first polypeptide consists of SEQ ID NO: 1.

15. The method of claim 7, wherein the first polypeptide consists of a variant of SEQ ID NO: 1 sharing at least 50% sequence identity therewith and differing from SEQ ID NO: 1 by one or more amino acid substitutions selected from the group consisting of V1I, V1L, V1A, V1G, V1T, V1S, V1M, E2D, E2K, E2R, D3E, T4G, T4S, T4Q, T4A, K5F, K5M, K5I, K5V, K5L, K5A, I6L, I6V, I6A, I6T, 165, I6Q, I6N, D7E, L8I, L8V, L8A, W9Y, S10T, S10G, S10A, S10M, and E14K.

16. The method of claim 15, wherein the variant has a sequence selected from the group consisting of SEQ ID NO: 3, SEQ ID NO: 4, SEQ ID NO: 5, SEQ ID NO: 6, SEQ ID NO: 8, SEQ ID NO: 9, SEQ ID NO: 10, and SEQ ID NO: 11.

17. An immunogenic peptide composition comprising a hemagglutinin fusion initiation region (FIR) peptide or a variant thereof bound to an influenza B hemagglutinin protein; wherein the FIR peptide has an amino acid sequence that consists of SEQ ID NO: 1 or a variant of SEQ ID NO: 1 sharing at least 50% sequence identity therewith and differing from SEQ ID NO: 1 by one or more amino acid substitutions selected from the group consisting of V1I, V1L, V1A, V1G, V1T, V1S, V1M, E2D, E2K, E2R, D3E, T4G, T4S, T4Q, T4A, K5F, K5M, K5I, K5V, K5L, K5A, I6L, I6V, I6A, I6T, I6S, I6Q, I6N, D7E, L8I, L8V, L8A, W9Y, S10T, S10G, S10A, S10M, and E14K.

18. A pharmaceutical composition for treating or preventing an influenza infection comprising the immunogenic peptide composition of claim 17 in a pharmaceutically acceptable carrier.

19. A method of treating an influenza infection comprising administering a therapeutically effective amount of the immunogenic peptide composition of claim 17 to a subject.

20. A method of inhibiting fusion of an influenza virus with the membrane of a host cell in a subject comprising administering the immunogenic peptide composition of claim 17 to the subject.

* * * * *

UNITED STATES PATENT AND TRADEMARK OFFICE
CERTIFICATE OF CORRECTION

PATENT NO. : 10,537,634 B2
APPLICATION NO. : 16/176743
DATED : January 21, 2020
INVENTOR(S) : Garry et al.

Page 1 of 1

It is certified that error appears in the above-identified patent and that said Letters Patent is hereby corrected as shown below:

In the Claims

Claim 15, Column 39, Line 1, delete "165" and insert --I6S--.

Signed and Sealed this
Twenty-fourth Day of March, 2020

Andrei Iancu
*Director of the United States Patent and Trademark Office*